US00PP23218P2

(12) United States Plant Patent
Hofmann

(10) Patent No.: US PP23,218 P2
(45) Date of Patent: Nov. 27, 2012

(54) ***VERBENA* PLANT NAMED 'INVEBROICH'**

(50) Latin Name: *Verbena hybrida*
Varietal Denomination: Invebroich

(75) Inventor: Birgit Hofmann, Rüdesheim am Rhein (DE)

(73) Assignee: Innova Plant GmbH + Co. KG, Gensingen (DE)

( * ) Notice: Subject to any disclaimer, the term of this patent is extended or adjusted under 35 U.S.C. 154(b) by 0 days.

(21) Appl. No.: 13/136,896

(22) Filed: Aug. 12, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — Howard Locker
(74) *Attorney, Agent, or Firm* — C. A. Whealy

(57) ABSTRACT

A new and distinct cultivar of *Verbena* plant named 'Invebroich', characterized by its semi-upright and outwardly spreading to trailing plant habit; moderately vigorous growth habit; freely branching habit; freely flowering habit; bright cherry red-colored flowers that are held above and beyond the foliar plane; and tolerance to mildew.

1 Drawing Sheet

Botanical designation: *Verbena hybrida*.
Cultivar denomination: 'INVEBROICH'.

BACKGROUND OF THE INVENTION

The present invention relates to a new and distinct cultivar of *Verbena* plant, botanically known as *Verbena hybrida*, and hereinafter referred to by the name 'Invebroich'.

The new *Verbena* plant is a product of a planned breeding program conducted by the Inventor in Gensingen, Germany. The objective of the breeding program is to create new freely-branching *Verbena* plants with numerous flowers and tolerance to mildew.

The new *Verbena* plant originated from a cross-pollination made by the Inventor during the summer of 2008 in Gensingen, Germany of a proprietary seedling selection of *Verbena hybrida* identified as code number Ve07-0001-6, not patented, as the female, or seed, parent with a proprietary seedling selection of *Verbena hybrida* identified as code number Ve07-0020-13, not patented, as the male, or pollen, parent. The new *Verbena* plant was discovered and selected by the Inventor as a single flowering plant within the progeny of the stated cross-pollination in a controlled environment in Gensingen, Germany during the spring of 2009.

Asexual reproduction of the new *Verbena* plant by terminal cuttings in a controlled environment in Gensingen, Germany since 2009 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Invebroich'. These characteristics in combination distinguish 'Invebroich' as a new and distinct *Verbena* plant:

1. Semi-upright and outwardly spreading to trailing plant habit.
2. Moderately vigorous growth habit.
3. Freely branching habit.
4. Freely flowering habit.
5. Bright cherry red-colored flowers that are held above and beyond the foliar plane.
6. Tolerant to mildew.

Plants of the new *Verbena* can be compared to plants of the female parent selection. Plants of the new *Verbena* differ primarily from plants of the female parent selection in the following characteristics:

1. Plants of the new *Verbena* are not as vigorous as plants of the female parent selection.
2. Plants of the new *Verbena* are more freely branching than plants of the female parent selection.
3. Plants of the new *Verbena* flower later than plants of the female parent selection.
4. Plants of the new *Verbena* and the female parent selection differ slightly in flower color.

Plants of the new *Verbena* can be compared to plants of the male parent selection. Plants of the new *Verbena* differ primarily from plants of the male parent selection in the following characteristics:

1. Plants of the new *Verbena* are more vigorous than plants of the male parent selection.
2. Plants of the new *Verbena* are more trailing than plants of the male parent selection.
3. Plants of the new *Verbena* are more freely branching than plants of the male parent selection.
4. Plants of the new *Verbena* flower later plants of the male parent selection.
5. Plants of the new *Verbena* and the male parent selection differ in flower color as plants of the male parent selection have apricot-colored flowers.

Plants of the new *Verbena* can be compared to plants of the *Verbena hybrida* 'AKIV5-4', disclosed in U.S. Plant Pat. No. 21,640. In side-by-side comparisons conducted in Bonsall, Calif., plants of the new *Verbena* differed primarily from plants of 'AKIV5-4' in the following characteristics:

1. Plants of the new *Verbena* were more compact than plants of 'AKIV5-4'.

2. Plants of the new *Verbena* were more trailing than plants of 'AKIV5-4'.
3. Plants of the new *Verbena* and 'AKIV5-4' differ in flower color as plants of 'AKIV5-4' have red-colored flowers.

Plants of the new *Verbena* can also be compared to plants of the *Verbena hybrida* 'Scarletta', disclosed in U.S. Plant Pat. No. 18,797. In side-by-side comparisons conducted in Bonsall, Calif., plants of the new *Verbena* differed primarily from plants of 'Scarletta' in the following characteristics:

1. Plants of the new *Verbena* were more trailing than plants of 'Scarletta'.
2. Plants of the new *Verbena* were not as vigorous as plants of 'Scarletta'.
3. Plants of the new *Verbena* had shorter internodes than plants of 'Scarletta'.
4. Plants of the new *Verbena* had smaller leaves than plants of 'Scarletta'.
5. Plants of the new *Verbena* and 'Scarletta' differed in flower color as plants of 'Scarletta' had scarlet red-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'Invebroich' grown in a container.

The photograph at the top of the sheet is a close-up view of a typical flowering plant of 'Invebroich'.

DETAILED BOTANICAL DESCRIPTION

Plants used for the aforementioned photographs and following description were grown under conditions which closely approximate commercial production conditions during the spring in 10-cm containers in a polyethylene-covered greenhouse in Bonsall, Calif. During the production of the plants, day temperatures averaged 27° C., night temperatures averaged 24° C. and light levels averaged 7,000 foot-candles. Plants were pinched two times and were 15 weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'Invebroich'.

Parentage:

*Female, or seed, parent*.—Proprietary seedling selection of *Verbena hybrida* identified as code number Ve07-0001-6, not patented.

*Male, or pollen, parent*.—Proprietary seedling selection of *Verbena hybrida* identified as code number Ve07-0020-13, not patented.

Propagation:

*Type cutting*.—Vegetative tip cuttings.

*Time to produce a rooted plant, summer*.—About 12 to 16 days at temperatures of about 25° C.

*Time to produce a rooted plant, winter*.—About 14 to 18 days at temperatures ranging from about 18° C. to 20° C.

*Root description*.—Medium in thickness, fibrous; white in color.

*Rooting habit*.—Moderately freely branching; medium in density.

Plant description:

*Plant and growth habit*.—Semi-upright and outwardly spreading to trailing plant habit; freely branching habit with about six to eight primary lateral branches developing per plant each with numerous secondary branches; pinching enhances lateral branch development; dense and bushy plant habit; moderately vigorous growth habit.

*Plant height*.—About 15.5 cm.

*Plant diameter* (*spread*).—About 20 cm by 24 cm.

Lateral branch description:

*Length*.—About 20 cm.

*Diameter*.—About 2 mm.

*Internode length*.—About 3 cm to 4 cm.

*Orientation*.—Initially upright then outwardly spreading to trailing.

*Strength*.—Strong.

*Texture*.—Pubescent.

*Color*.—Close to 146C.

Foliage description:

*Arrangement*.—Opposite, simple.

*Length*.—About 4.4 cm.

*Width*.—About 2.7 cm.

*Shape*.—When developing, slightly deltoid then becoming more elliptical with narrow rounded lobing.

*Apex*.—Broadly acute.

*Base*.—Attenuate.

*Margin*.—Narrow rounded lobing.

*Texture, upper and lower surfaces*.—Pubescent; coarse, bristly.

*Venation pattern*.—Pinnate; reticulate.

*Color*.—Developing and fully expanded leaves, upper surface: Close to 137A; venation, close to 147C. Developing and fully expanded leaves, lower surface: Close to 147B; venation, close to 148D.

*Petiole*.—Length: About 1.7 cm. Diameter: About 2.5 mm. Texture, upper and lower surfaces: Pubescent. Color, upper surface: Close to 145C. Color, lower surface: Close to 147D.

Flower description:

*Flower arrangement and habit*.—Sessile salverform flowers arranged in compact hemispherical terminal racemes; flowers face upward or outwardly; freely flowering habit with about 54 flowers developing per inflorescence.

*Natural flowering season*.—Plants flower continuously from spring through the autumn in California; plants begin flowering about ten weeks after planting.

*Flower longevity*.—Flowers last about five to seven days on the plant; flowers not persistent.

*Fragrance*.—None detected.

*Inflorescence height*.—About 3.4 cm.

*Inflorescence diameter*.—About 4.7 cm.

*Flower diameter*.—About 1.3 cm.

*Flower depth* (*height*).—About 2.1 cm.

*Throat diameter*.—About 1.5 mm.

*Tube length*.—About 1.8 cm.

*Tube diameter, proximal*.—About 2 mm.

*Flower buds*.—Length: About 1.7 cm. Diameter: About 4 mm. Shape: Elongated oblong. Color: Close to 63D.

*Corolla*.—Arrangement: Single whorl of five fused petals fused towards the base into a narrow tube. Petal lobe length: About 4 mm. Petal lobe width: About 6 mm. Petal lobe shape: Roughly cordate. Petal lobe apex: Emarginate. Petal margin: Entire. Petal texture, upper surface: Smooth, glabrous. Petal texture, lower surface: Sparsely pubescent. Throat texture: Pubescent. Tube texture: Sparsely pubescent. Color: Petal, when opening, upper surface: Close to 53C. Petal, when opening, lower surface: Close to 64D. Petal, fully opened, upper surface: Close to 53C; with development, color becoming closer to 54A; venation, close to 53C. Petal, fully opened, lower surface: Close to 54A to 54B; venation, close to 54A. Throat: Close to 195D; venation, close to 195C. Tube: Close to 195C; venation, close to 195C.

*Calyx*.—Arrangement: Single whorl of five fused sepals fused towards the base into a narrow tube. Sepal length: About 1.1 cm. Sepal width: About 1 mm. Sepal shape: Narrowly lanceolate. Sepal apex: Acute. Sepal margin: Entire. Sepal texture, inner surface: Smooth, glabrous. Sepal texture, outer surface: Pubescent. Sepal color, upper surface: Close to 195B. Sepal color, lower surface: Close to 191A.

*Peduncles*.—Length: About 3.6 cm. Diameter: About 2 mm. Strength: Strong. Texture: Pubescent. Color: Close to 137C.

*Reproductive organs*.—Stamens: Quantity/arrangement: Four per flower, filaments are adnate to corolla tube. Filament length, free section: About 1 mm. Filament color: Close to 145C. Anther shape: Oval, bilobed. Anther length: About 1.5 mm. Anther color: Close to 153C. Pollen amount: Scarce. Pollen color: Close to 153D. Pistils: Quantity: One per flower. Pistil length: About 1.9 cm. Stigma shape: Rounded, slightly bi-parted. Stigma color: Close to 145A. Style length: About 1.6 cm. Style color: Close to 145D. Ovary color: Close to 194D.

*Fruits and seeds*.—Fruit and seed development have not been observed on plants of the new *Verbena*.

Temperature tolerance: Plants of the new *Verbena* have been observed to tolerate temperatures from about 1° C. to about 40° C.

Pathogen/pest resistance: Plants of the new *Verbena* have been observed to be tolerant to mildew. Plants of the new *Verbena* have not been observed to be resistant to pests and other pathogens common to *Verbena* plants.

It is claimed:

1. A new and distinct *Verbena* plant named 'Invebroich' as illustrated and described.

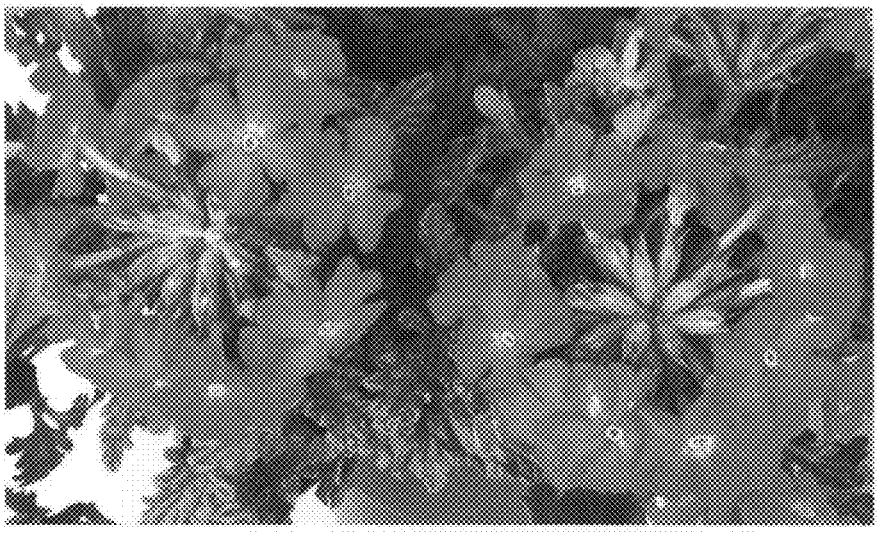
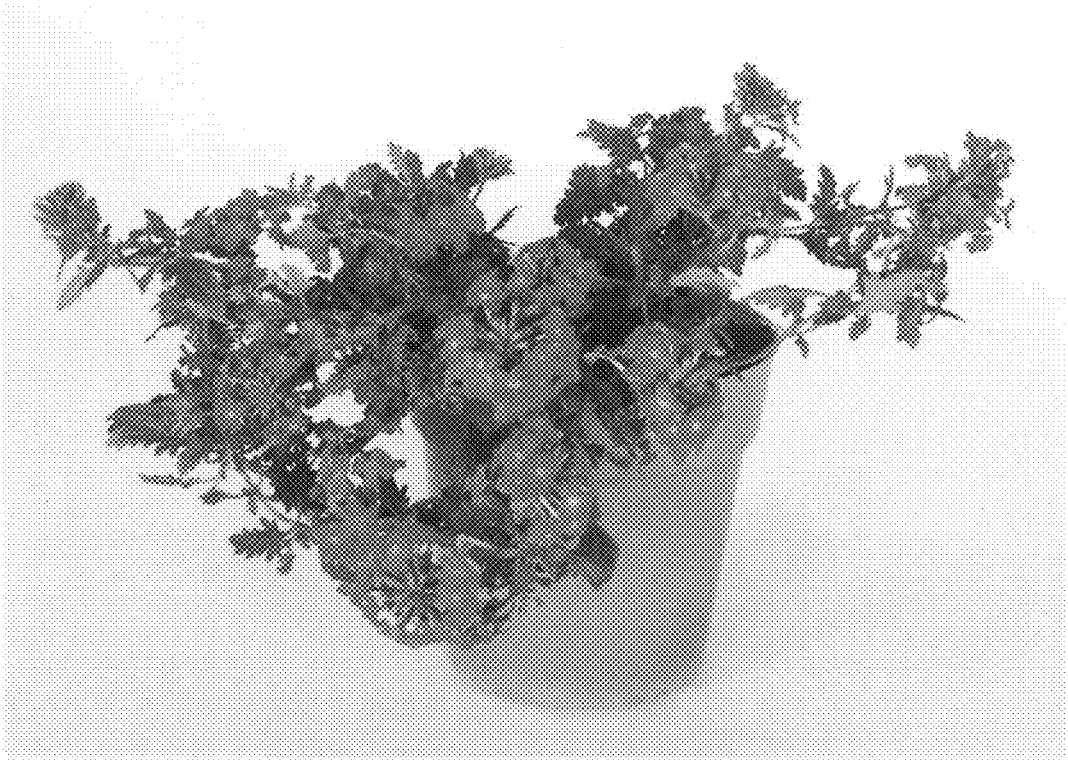

* * * * *